US010751539B2

(12) United States Patent
Von Zitzewitz et al.

(10) Patent No.: US 10,751,539 B2
(45) Date of Patent: Aug. 25, 2020

(54) ACTIVE CLOSED-LOOP MEDICAL SYSTEM

(71) Applicant: GTX medical B.V., Eindhoven (NL)

(72) Inventors: Joachim Von Zitzewitz, Eindhoven (NL); Vincent Delattre, Eindhoven (NL); Bert Bakker, Eindhoven (NL); Grégoire Courtine, Eindhoven (NL)

(73) Assignee: GTX MEDICAL B.V., Eindhoven (NL)

( * ) Notice: Subject to any disclaimer, the term of this patent is extended or adjusted under 35 U.S.C. 154(b) by 55 days.

(21) Appl. No.: 15/814,235

(22) Filed: Nov. 15, 2017

(65) Prior Publication Data

US 2018/0133481 A1     May 17, 2018

(30) Foreign Application Priority Data

Nov. 16, 2016 (EP) .................................. 16199094

(51) Int. Cl.
*A61N 1/36* (2006.01)
*A61N 1/372* (2006.01)
(Continued)

(52) U.S. Cl.
CPC ............ *A61N 1/36139* (2013.01); *A61B 5/01* (2013.01); *A61B 5/04001* (2013.01);
(Continued)

(58) Field of Classification Search
CPC ..... A61B 5/01; A61B 5/04001; A61B 5/0488; A61B 5/11; A61B 5/4836; A61N 1/025;
(Continued)

(56) References Cited

U.S. PATENT DOCUMENTS 6,058,331 A * 5/2000 King .................... A61N 1/3605
607/2
6,878,112 B2   4/2005 Linberg et al.
(Continued)

FOREIGN PATENT DOCUMENTS

EP     2868343 A1   5/2015
WO    0234331 A2   5/2002
(Continued)

OTHER PUBLICATIONS

Guyatt, G. et al., "The 6-minute walk: a new measure of exercise capacity in patients with chronic heart failure," Canadian Medical Association Journal, vol. 132, No. 8, Apr. 15, 1985, 5 pages.
(Continued)

*Primary Examiner* — George Manuel
(74) *Attorney, Agent, or Firm* — McCoy Russell LLP

(57) ABSTRACT

The present disclosure relates to an active closed-loop medical system comprising at least one implantable medical device, at least one non-implanted component and at least a controller for controlling the implantable medical device, wherein the implantable medical device, the non-implanted component and the controller are connected for data exchange, wherein the implantable medical device, the non-implanted component and the controller forming in the active state a closed-loop system in such that the implantable medical device is controlled by the controller on the basis of the signals exchanged with the non-implanted component.

19 Claims, 3 Drawing Sheets

(51) Int. Cl.
| | |
|---|---|
| A61B 5/01 | (2006.01) |
| A61B 5/04 | (2006.01) |
| A61B 5/11 | (2006.01) |
| A61B 5/00 | (2006.01) |
| A61N 1/05 | (2006.01) |
| A61N 1/02 | (2006.01) |
| A61B 5/0488 | (2006.01) |

(52) U.S. Cl.
CPC .............. *A61B 5/0488* (2013.01); *A61B 5/11* (2013.01); *A61B 5/4836* (2013.01); *A61N 1/025* (2013.01); *A61N 1/0551* (2013.01); *A61N 1/36062* (2017.08); *A61N 1/36103* (2013.01); *A61N 1/37217* (2013.01); *A61N 1/36135* (2013.01); *A61N 1/37247* (2013.01)

(58) Field of Classification Search
CPC .............. A61N 1/0551; A61N 1/36062; A61N 1/36103; A61N 1/36135; A61N 1/36139; A61N 1/37217; A61N 1/37247
See application file for complete search history.

(56) References Cited

U.S. PATENT DOCUMENTS

| | | | |
|---|---|---|---|
| 7,149,773 | B2 | 12/2006 | Haller et al. |
| 7,742,037 | B2 | 6/2010 | Sako et al. |
| 8,326,569 | B2 | 12/2012 | Lee et al. |
| 2002/0052539 | A1 | 5/2002 | Haller et al. |
| 2005/0061315 | A1* | 3/2005 | Lee ...................... A61B 5/0031 128/200.24 |
| 2005/0277999 | A1* | 12/2005 | Strother ............... A61B 5/0031 607/48 |
| 2007/0004567 | A1 | 1/2007 | Shetty et al. |
| 2010/0114205 | A1* | 5/2010 | Donofrio ................. A61N 1/08 607/4 |
| 2014/0180361 | A1* | 6/2014 | Burdick ............... A61N 1/0553 607/49 |

FOREIGN PATENT DOCUMENTS

| | | |
|---|---|---|
| WO | 2007047852 A2 | 4/2007 |
| WO | 2012080964 A1 | 6/2012 |

OTHER PUBLICATIONS

Lovely, R. et al., "Effects of Training on the Recovery of Full-Weight-Bearing Stepping in the Adult Spinal Cat," Experimental Neurology, vol. 92, No. 2, May 1986, 15 pages.

Barbeau, H. et al., "Recovery of locomotion after chronic spinalization in the adult cat," Brain Research, vol. 412, No. 1, May 26, 1987, 12 pages.

Colgate, E. et al., "An Analysis of Contact Instability in Terms of Passive Physical Equivalents," Proceedings of the 1989 IEEE International Conference on Robotics and Automation, May 14, 1989, Scottsdale, Arizona, 6 pages.

Wernig, A. et al., "Laufband locomotion with body weight support improved walking in persons with severe spinal cord injuries," Paraplegia, vol. 30, No. 4, Apr. 1992, 10 pages.

Winter, D. et al., "An integrated EMG/biomechanical model of upper body balance and posture during human gait," Progress in Brain Research, vol. 97, Chapter 32, Available as Early as Jan. 1, 1993, 9 pages.

Wernig, A. et al., "Laufband Therapy Based on 'Rules of Spinal Locomotion' is Effective in Spinal Cord Injured Persons," European Journal of Neuroscience, vol. 7, No. 4, Apr. 1995, 7 pages.

Pratt, G. et al., "Stiffness Isn't Everything," Proceedings of the Fourth International Symposium on Experimental Robotics (ISER '95), Jun. 30, 1995, Stanford, California, 6 pages.

Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.

Harkema, S. et al., "Human Lumbosacral Spinal Cord Interprets Loading During Stepping," Journal of Neurophysiology, vol. 77, No. 2, Feb. 1, 1997, 15 pages.

Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.

Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.

Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.

Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Aug. 1, 2000, Published Online Jul. 17, 2000, 2 pages.

Pratt, J. et al., "Series elastic actuators for high fidelity force control," Industrial Robot: An International Journal, vol. 29, No. 3, Available as Early as Jan. 1, 2002, 13 pages.

Steward, O. et al. "False Resurrections: Distinguishing Regenerated from Spared Axons in the Injured Central Nervous System," The Journal of Comparative Neurology, vol. 459, No. 1, Apr. 21, 2003, 8 pages.

Pearson, K., "Generating the walking gait: role of sensory feedback," Progress in Brain Research, vol. 143, Chapter 12, Published Online Nov. 28, 2003, 7 pages.

Bareyre, F. et al., "The injured spinal cord spontaneously forms a new intraspinal circuit in adult rats," Nature Neuroscience, vol. 7, No. 3, Mar. 2004, Published Online Feb. 15, 2004, 9 pages.

Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 15, 2004, 11 pages.

Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Aug. 1, 2005, Published Online May 4, 2005, 13 pages.

Timoszyk, W. et al., "Hindlimb loading determines stepping quantity and quality following spinal cord transection," Brain Research, vol. 1050, No. 1-2, Jul. 19, 2005, Published Online Jun. 24, 2005, 10 pages.

Wernig, A., "'Ineffectiveness' of Automated Locomotor Training," Archives of Physical Medicine and Rehabilitation, vol. 86, No. 12, Dec. 2005, 2 pages.

Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.

Reinkensmeyer, D. et al., "Tools for understanding and optimizing robotic gait training," Journal of Rehabilitation Research & Development, vol. 43, No. 5, Aug. 2006, 14 pages.

Frey, M. et al., "A Novel Mechatronic Body Weight Support System," IEEE Transactions on Neural Systems and Rehabilitation Engineering, vol. 14, No. 3, Sep. 18, 2006, 11 pages.

Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.

Courtine, G. et al., "Can experiments in nonhuman primates expedite the translation of treatments for spinal cord injury in humans?," Nature Medicine, vol. 13, No. 5, May 2007, 13 pages.

Drew, T. et al., "Cortical mechanisms involved in visuomotor coordination during precision walking," Brain Research Reviews, vol. 57, No. 1, Jan. 2008, Published Online Aug. 22, 2007, 13 pages.

(56) References Cited

OTHER PUBLICATIONS

Edgerton, V. et al., "Training Locomotor Networks," Brain Research Reviews, vol. 57, No. 1, Jan. 2008, Published Online Sep. 16, 2007, 25 pages.
Kwakkel, G. et al., "Effects of Robot-assisted therapy on upper limb recovery after stroke: A Systematic Review," Neruorehabilitation and Neural Repair, vol. 22, No. 2, Mar. 2008, Published Online Sep. 17, 2007, 17 pages.
Courtine, G. et al., "Recovery of supraspinal control of stepping via indirect propriospinal relay connections after spinal cord injury," Nature Medicine, vol. 14, No. 1, Jan. 6, 2008, 6 pages.
Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Vallery, H. et al., "Compliant Actuation of Rehabilitation Robots," IEEE Robotics & Automation Magazine, vol. 15, No. 3, Sep. 12, 2008, 10 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Fuentes, R. et al., "Spinal Cord Stimulation Restores Locomotion in Animal Models of Parkinson's Disease," Science, vol. 323, No. 5921, Mar. 20, 2009, 14 pages.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.
Alto, L. et al "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.
Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, Jun. 2010, 7 pages.
Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.
Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.
Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.
Hidler, J. et al., "ZeroG: Overground gait and balance training system," Journal of Rehabilitation Research & Development, vol. 48, No. 4, Available as Early as Jan. 1, 2011, 12 pages.
Musselman, K. et al., "Spinal Cord Injury Functional Ambulation Profile: A New Measure of Walking Ability," Neurorehabilitation and Neural Repair, vol. 25, No. 3, Mar. 2011, Published Online Feb. 25, 2011, 9 pages.
Harkema, S. et al., "Effect of Epidural stimulation of the lumbosacral spinal cord on voluntary movement, standing, and assisted stepping after motor complete paraplegia: a case study," The Lancet, vol. 377, No. 9781, Jun. 4, 2011, Published Online May 20, 2011, 17 pages.
Wirz, M. et al., "Effectiveness of automated locomotor training in patients with acute incomplete spinal cord injury: A randomized controlled multicenter trial," BMC Neurology, vol. 11, No. 60, May 27, 2011, 5 pages.
Musienko, P. et al., "Controlling specific locomotor behaviors through multidimensional monoaminergic modulation of spinal circuitries," The Journal of Neuroscience, vol. 31, No. 25, Jun. 22, 2011, 32 pages.
Musienko, P. et al. "Multi-system neurorehabilitative strategies to restore motor functions following severe spinal cord injury," Experimental Neurology, vol. 235, No. 1, May 2012, Published Online Sep. 7, 2011, 10 pages.
Sun, F. et al., "Sustained axon regeneration induced by co-deletion of PTEN and SOCS3," Nature, vol. 480, No. 7377, Dec. 15, 2011, Published Online Nov. 6, 2011, 12 pages.
Courtine, G. et al., "Transformation of nonfunctional spinal circuits into functional states after the loss of brain input," Nature Neuroscience, vol. 12, No. 10, Oct. 2009, Published Online Sep. 20, 2009, 20 pages.
Capogrosso, M. et al., "A Computational Model for Epidural Electrical Stimulation of Spinal Sensorimotor Circuits," The Journal of Neuroscience, vol. 33, No. 49, Dec. 4, 2013, 15 pages.
Wenger, N. et al., "Closed-loop neuromodulation of spinal sensorimotor circuits controls refined locomotion after complete spinal cord injury," Science Translational Medicine, vol. 6, No. 255, Sep. 24, 2014, 10 pages.
Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Published Online Feb. 4, 2016, 15 pages.

\* cited by examiner

ACTIVE CLOSED-LOOP MEDICAL SYSTEM

CROSS REFERENCE TO RELATED APPLICATIONS

This application claims priority to European Patent Application No. 16199094.0, entitled "An Active Closed-Loop Medical System," filed Aug. 16, 2016, the entire contents of which are hereby incorporated by reference for all purposes.

TECHNICAL FIELD

The present disclosure relates to an active closed-loop medical system, especially an active closed-loop medical system for neurostimulation, e.g. in the field of improving recovery after neurological disorders like spinal cord injury (SCI), for example after trauma.

BACKGROUND AND SUMMARY

EP 2 868 343 A1 discloses a system to deliver adaptive electrical spinal cord stimulation to facilitate and restore locomotion after neuromotor impairment. Inter alia, a closed-loop system for real-time control of epidural electrical stimulation is disclosed, comprising means for applying to a subject neuromodulation with adjustable stimulation parameters, means being operatively connected with a real-time monitoring component comprising sensors continuously acquiring feedback signals from subject, signals providing features of motion of a subject, system being operatively connected with a signal processing device receiving feedback signals and operating real-time automatic control algorithms, signal processing device being operatively connected with means and providing means with new stimulation parameters, with minimum delay. The system of the present disclosure improves consistency of walking in a subject with a neuromotor impairment. A Real Time Automatic Control Algorithm is used, comprising a feedforward component employing a single input-single output model (SISO), or a multiple input-single output (MISO) model. Reference is also made to Wenger et al., Closed-loop neuromodulation of spinal sensorimotor circuits controls refined locomotion after complete spinal cord injury, in Science Translational Medicine, vol. 6, num. 255, 2014.

WO 2002/034331 A2 discloses a non-closed loop implantable medical device system that includes an implantable medical device, along with a transceiver device that exchanges data with the patient, between the patient and the implantable medical device, and between a remote location and the implantable medical device. A communication device coupled to the transceiver device exchanges data with the transceiver device, the implantable medical device through the receiver device, and between the transceiver device and the remote location to enable bi-directional data transfer between the patient, the implantable medical device, the transceiver device, and the remote location. A converter unit converts transmission of the data from a first telemetry format to a second telemetry format, and a user interface enables information to be exchanged between the transceiver device and the patient, between the implantable medical device and the patient through the transceiver device, and between the patient and the remote location through the transceiver device.

US 2002/0052539 A1 describes a partial closed loop, non-continuous and non-real-time emergency medical information communication system and corresponding methods. The system permits an emergency alert to be issued on the basis of information sensed or processed by an implantable medical device (IMD) implanted within a body of a patient. The IMD is capable of bidirectional communication with a communication module, a mobile telephone and/or a Personal Data Assistant (PDA) located outside the patient's body. The communication module, a mobile telephone or a PDA is capable of communicating an emergency alert generated by the IMD to a remote computer via a communication system. At the remote computer system it may be determined that emergency remedial action is required. If so, the action is executed remotely from the remote computer system in the IMD via the communication system.

U.S. Pat. No. 7,149,773 B2 relates to methods, devices and systems for automatically generating invoices when medical services are provided to a patient are described. Invoices are automatically generated by the system, for example, when monitoring of certain aspects of the performance of an implantable medical device (IMD) implanted within a body of a patient is initiated by the patient or remotely, or when the delivery of a therapy to the patient through the IMD is initiated locally or remotely. The IMD is capable of bi-directional communication with a communication module, a mobile telephone and/or a Personal Data Assistant (PDA) located outside the patient's body. The system invoicing system may comprise the IMD, the communication module and/or a mobile telephone and/or a PDA, means for generating an invoice, a remote computer system, and a communication system capable of bi-directional communication, where the communication module, the mobile telephone and/or the PDA is capable of receiving information from the IMD or relaying information thereto.

U.S. Pat. No. 6,878,112 B2 discloses a plurality of co-operative and complementary software programs are implemented in a web-enabled high speed computer system to remotely monitor, manage and modify the operational and functional parameters of a plurality of implanted medical devices (IMDs). The system utilizes virtual electrophysiologist module (VEM), chronic monitoring module (CMM) and prescription program module (PPM) programs to effect specific therapeutic and diagnostic methods for managing the IMDs, remotely on a conditions and real-time basis. The modules enable remote and continuous monitoring, management and maintenance of the IMDs by identifying critical medical events, determining optimal clinical settings and upgrading performance parameters based on prescriptive data. The modules are implemented in a data center having high-speed computers operating in a web-enabled environment. The modules and the IMDs communicate through wireless communications system via a programmer or an interface medical unit (IMD).

EP 2 652 676 A1 relates to a gesture controlling for monitoring vital body signs and reuses an accelerometer, or, more precise, sensed accelerations of a body sensor for user control of the body sensor. This is achieved by detecting predefined patterns in the acceleration signals that are unrelated to other movements of the patient. These include tapping on/with the sensor, shaking, and turning the sensor. New procedures are described that make it possible to re-use the acceleration sensing for reliable gesture detection without introducing many false positives due to non-gesture movements like respiration, heart beat, walking, etc. Similar solutions for tapping detection of a user are known from U.S. Pat. Nos. 8,326,569 and 7,742,037.

Epidural Electrical Stimulation (EES) is known as a different approach to Functional Electrical Stimulation (FES). Several scientific papers deal with EES, e.g. Capogrosso, M, et al., A Computational Model for Epidural Electrical Stimulation of Spinal Sensorimotor Circuits, Journal of Neuroscience 4 Dec. 2013, 33 (49) 19326-19340, Courtine et al., Transformation of nonfunctional spinal circuits into functional states after the loss of brain input, Nat Neurosci. 2009 October; 12(10): 1333-1342. Moraud et al, Mechanisms Underlying the Neuromodulation of Spinal Circuits for Correcting Gait and Balance Deficits after Spinal Cord Injury, Neuron Volume 89, Issue 4, p 814-828, 17 Feb. 2016.

It is an object of the present disclosure to provide an active closed-loop medical system with enhanced functionality, especially an active closed-loop medical system for neurostimulation, e.g. in the field of improving recovery after neurological disorders like spinal cord injury (SCI), for example after trauma, especially in that a closed-loop system can established not only on the basis of implanted components.

This object is solved according to the present disclosure by an active closed-loop medical system with the features of claim 1. Accordingly, an active closed-loop medical system is provided comprising at least one implantable medical device, at least one non-implanted component and at least a controller for controlling the implantable medical device, wherein the implantable medical device, the non-implanted component and the controller are connected for information exchange, wherein the implantable medical device, the non-implanted component and the controller form in the active state a closed-loop system in such that the implantable medical device is controlled by the controller on the basis of the signals exchanged with the non-implanted component.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
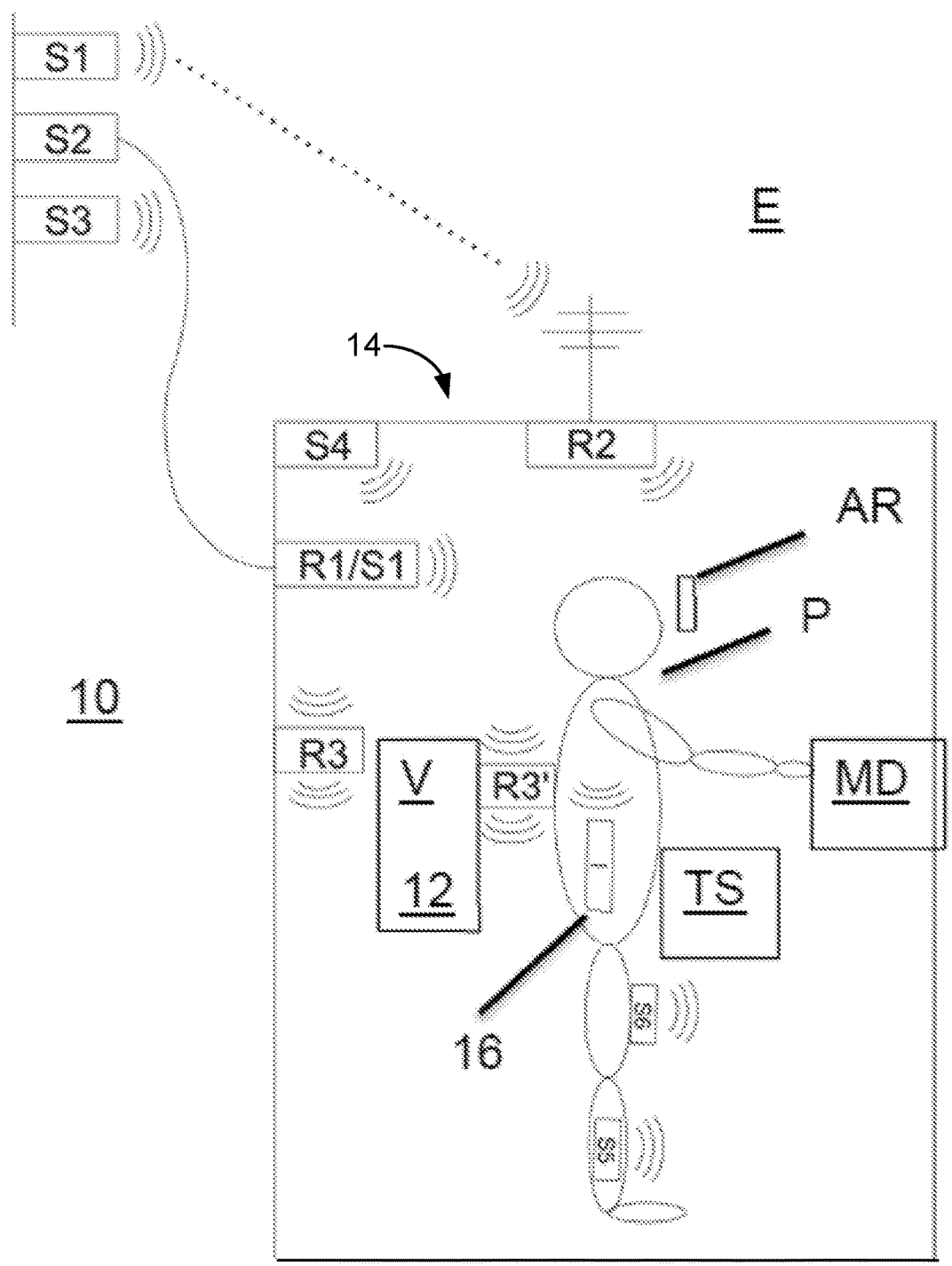
FIG. 1 shows a schematic view of an active closed-loop medical system in a training environment.
Figure 2:
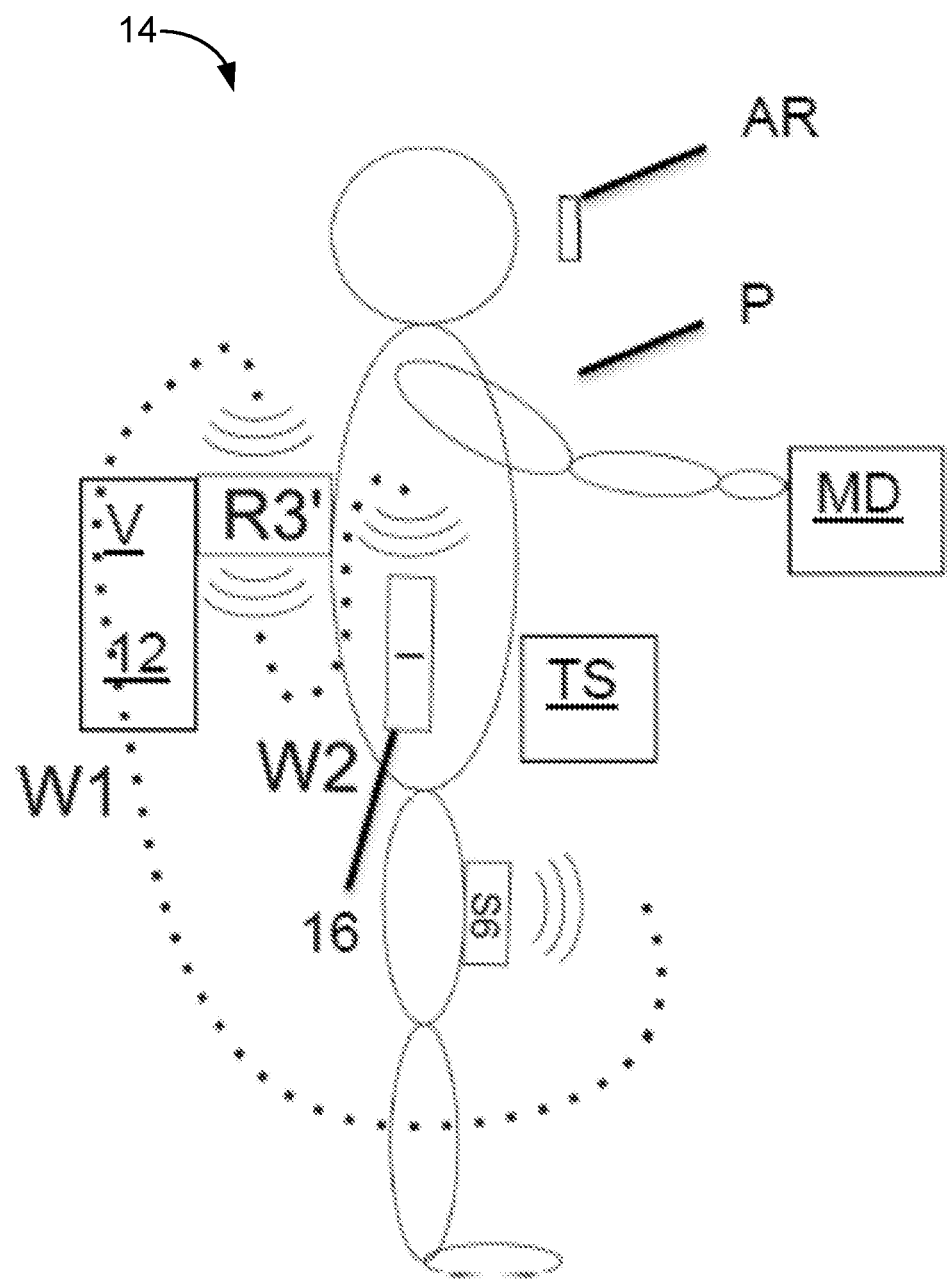
FIG. 2 shows the active closed-loop medical system, as shown in FIG. 1, outside of the training environment.

The following description relates to systems and methods for an active, closed-loop medical system, such as the system shown in FIGS. 1 and 2. The system may include an implantable medical device, such as an implantable pulse generator or a neurostimulator, a controller, and one or more external sensors positioned on or around a patient in which the implantable medical device is implanted. During operation, the control signals sent to the implantable medical device may be determined and updated according to motion feedback signals received by the one or more sensors during stimulation of the patient, as shown in the example method presented at FIG. 3. In this way, more accurate stimulation signals may be delivered to a patient, thereby increasing the effectiveness of their treatment and recovery.

The present disclosure is based on the basic idea that components of the closed-loop system are connected to each other, irrespective of whether they are inside, i.e. implanted in the patient, or outside, i.e. designed as wearable or attached to the body of the patient, of the body of the patient. By means of the connection of the components of the system, a data exchange can be done, which is needed to form a closed-loop system. This means inter alia, that components of the closed-loop system interact in order to control signals with at least another component of the closed-loop system and that also at least one component gives feedback to for example the controlling means of the closed loop system in order to influence the next and upcoming control signals to be provided by the controlling means. Also, components can be arranged inside and outside of e.g. the human body of a patient to be treated. This allows a design, where only those components must be implanted into the patient that are really necessary within the patient, e.g. as implantable medical device an implantable pulse generator, a neurostimulator or neuromodulator. Components, that might need maintenance over the lifetime like battery exchange, sensor or sensor battery exchange, regular recharging, new set up of control data or software updates can now be arranged outside of the body of the patient. Consequently, an active closed-loop medical system for e.g. neurostimulation (but not limited to this field) may be provided, e.g. in the field of improving recovery after neurological disorders like spinal cord injury (SCI), for example after trauma, or other conditions like stroke or multiple sclerosis, especially in that a closed-loop system can established not only on the basis of implanted components.

For example, the implantable medical device can comprise or be a neurostimulator.

In particular, it is possible that the implantable medical device comprises or is a neurostimulator or a component of a neurostimulator, especially wherein the neurostimulator is a Epidural Electrical Stimulation (EES) neurostimulator.

Epidural Electrical Stimulation (EES) does not directly stimulate motor-neurons but the afferent sensory neurons prior to entering into the spinal cord, hence activating the synaptic circuits that are naturally involved in locomotor control. Therefore, EES specifically triggers activity dependent plasticity in the spinal cord resulting in ongoing learning and improvement of the patient's locomotor function. This stimulation mode mediates a continuous activation of all the proprioceptive afferent nerves at the same time.

EES may be used to further improve immediate and training-induced effects can be further improved when proprioceptive afferent nerves are stimulated more selectively and aligned with the different phases of the gait cycle. During walking, these phases consist of an alternation between stimulation of the extension and flexion muscles of the right versus the left leg. Time-space EES may be used to restore both the swing phase (flexion) and the weight-bearing stance phase (extension) whereas continuous EES may block the limbs.

To the contrary, during Functional Electrical Stimulation (FES), efferent motor-neuron axons and muscles are stimulated directly and distally from the complex synaptic circuits of the spinal cord that regulate the locomotors activities. Consequently, the resulting movements and muscular activities are involuntary and do not trigger as much plasticity mechanisms in the spinal cord that allow for learning an improvement of the locomotor functions over time. Conceptually, FES complies the same principles as discovered by Luigi Galvani in 1780 by inducing muscle contractions in frogs. Summarizing, FES makes use of the basic principles of electro-physiology and therefore can lead to easily obtain immediate successes. However, long clinical history has shown that successes remain isolated cases and that the combination of cumbersome stimulation with the immediate muscle fatigue renders FES unsuitable for use in daily life especially in the field where the patent application is aiming for. The more recently discovered indirect EES method builds on a strong scientific foundation and has the potential to overcome the most of the inherent limitation to FES but is lacking larger clinical experience so far.

In particular, the Epidural Electrical Stimulation (EES) neurostimulator may be arranged and configured as a spatially selective spinal implant, configured to work on the basis of temporally precise stimulation algorithms adjusted in a 'closed-loop' way using real-time motion feedback inputs as a part of the active closed-loop medical system.

It is possible that the non-implanted component and the controlling means are connected at least partially wirelessly and/or by means of a wired connection. The idea behind is that the most suitable and/or reliable connection should and can be established.

A wireless connection provides more degrees of freedom and liberty of action.

A wired connection is very reliable and less prone to external factors like disturbing and interfering signals.

The combination of both a wireless connection and wired connection can be advantageous in order to realize a good combination in terms of more degrees of freedom and liberty of action and reliability at the same time. So, redundant data connection can be established.

The controlling means may be configured such that the signals exchanged with the controlling means from the non-implanted component and/or the implantable medical device are processed in real-time.

Real-time may be understood as real-time or close to real-time. Inter alia, a time frame and short delay between 0.0 to approximately 30 ms can be understood to fulfill the condition real-time.

For example, the data exchange between the controlling means and the implantable medical device may be such that the controlling means and at least one component of implantable medical device exchange signals. The at least one component may be for example an implantable or implanted sensor.

The signals may include and/or may be related inter alia to data such as system data and/or patient data and/or physiological data. Moreover, the signals may be related to control data and/or information or the like.

A processing of the signals received by the controlling means from the non-implanted component is of advantage to enhance the performance of the active closed-loop medical system. Such a real-time processing allows significant improvements in the field of neurostimulation, in particular that based on sensor input in real-time or close to real-time the necessary signals may be prepared based on the processing of the input sensor signals.

The controlling means may be at least partially arranged extra corporeal. This simplifies the maintenance of the controlling means. Furthermore, a battery change for the controlling means may be made easier by having the controlling means at least partially arranged extra corporeally.

The controlling means may be at least partially arranged intra corporeal. In particular this part of the controlling means may be for example an electronic component that is part of the implantable medical device. The intra corporeal part of the controlling means may be also simply a communication module that is able to communicate with the extra corporeal part of the controlling means.

The non-implanted component may comprise or may be a sensor for sensing physiological data of the user of the active closed-loop medical system. Such a sensor may be chosen from the group of gyroscopes, accelerometers, video cameras, pressure sensors, force sensors, electromyograms (EMG), neural probes or the like. Such sensors may for example detect motion features like kinetics, kinematics, muscular activity, neuronal signals, movement of the patient, intended movement of the patient or the like. The physiological data may be related to electrophysiological signals especially related to movement of the patient.

The active closed-loop medical system may further comprise at least one implanted sensor as a part of the implantable medical devise for sensing physiological data of the user of the active closed-loop medical system. The physiological data may be related to electrophysiological signals especially related to movement of the patient. By this, very specific signals may be detected and alternatively or in combination with sensors outside of the body and the triggering events for the intended motor tasks, for example locomotion, may be detected and used for the control signals provided by the controlling means.

The sensor(s) may be configured to acquire signals related to physiological data including but not limited to motion, kinetics, kinematics, muscular activity, neural activity, neural activity correlates, body temperature.

The system may comprise a voice control module configured to receive and process voice based commands that set the specific control signals and/or method steps of the closed-loop processing of the system, especially to stand and/or walk and/or sit to stand/stand up, move the arms and/or generally move parts of the body. The system and especially the voice control module may comprise or may be a sensor for example for detection of voice based commands that set the specific control signals and program features of the closed-loop processing, for example to stand, walk, sit to stand, move the arms and/or generally move parts of the body. Also, if applicable, the non-implanted and/or implanted sensor (e.g. provided as part of the implantable medical device) may be a sensor for example for detection of voice based commands that set the specific control signals and program features of the closed-loop processing, for example to stand, walk, sit to stand, move the arms and/or generally move parts of the body. By providing a voice control the handling of the whole system for the user is simplified and can be more intuitive. Especially in cases, when the patient or the physician or the trainer of the patient intends to change the way or kind of movement, this can be triggered by a simple voice command. Such a voice command is then received by the voice control module, transformed into a system signal configured to be processed by controlling means and submitted to the controlling means. This process may be done also in real-time.

A voice recognition provides more degrees of freedom and liberty of action, especially for individuals with limited arm and hand mobility due to neurological disorders like spinal cord injury (SCI), for example after cervical spinal cord trauma.

Voice recognition is especially very useful for the treatment of tetraplegic patients. By using voice commands, such patients will be enabled to control intuitively and very easily the system.

The active closed-loop medical system may comprise extra corporeal communication means, wherein the extra corporeal communication means comprise a receiver, which is connected in the active state with the non-implanted component. By means of the receiver the extra corporeal communication means is capable to establish a connection with the non-implanted components and a subset of implanted components, e.g. such as the sensors or the like.

Furthermore, the implantable medical device may have an intra corporeal data transmission unit comprising a data transmission coil, wherein the receiver also comprises a data transmission coil and wherein the receiver in the intercorporeal data transmission unit transcutaneous connected by means of a coil-to-coil-communication connection provided by the data transmission coil of the receiver and the inter corporeal data transmission unit.

The coil-to-coil-communication connection may be an inductive coupling, which can be used to transfer data but also energy. This can provide a reliable and highly efficient communication connection for transcutaneous data and/or energy transmission from the extra corporeal parts of the active closed-loop medical system to the intra corporeal parts of the active closed-loop medical system. The communication may be bi-directional. It is possible that for each communication direction a separate coil-to-coil-communication is established.

Generally speaking, alternatives to a coil-to-coil-communication connection any suitable inductive coupling or inductive coupled link may be used.

Furthermore, the receiver may be connected in the active state with the non-implanted component via Bluetooth and/or WIFI. Generally speaking, other suitable wireless data transfer protocols may be used. Alternatively, for example optical means, RF-technology or inductive coupling or magnetic field technology or ultrasound can be used.

Bluetooth and/or WIFI data connections may, in one example, be used and provide the advantage that a fast data transmission, which is bi-directional and real-time or close to real-time, can be provided.

Voice may, one example, be used and provide the advantage of a fast and simple transmission of instruction to the external controller.

The receiver may be connected in the active state with the implanted or the non-implanted component via a wireless ultrasound link. For example, the receiver and the implanted, or respectively the non-implanted, component can be configured such that both components of the active closed-loop medical system are able to modulate the ultrasound to carry a signal (like radio signals are modulated). Furthermore, both components of the active closed-loop medical system may be configured that the received ultrasound signal may be decoded by a modulated-ultrasound receiver being part of the receiver and also part of the implanted, or respectively the non-implanted, component or any other suitable signal. This signal may then be used for inter alia controlling the overall system in real-time.

Additionally, the communication of the components of the active closed-loop medical system may be bi-directional. To enhance and to improve the functionality of the active closed-loop medical system bi-directional communication of the components of the active close-loop medical system is wanted. Inter alia, direct feedback on the control signals is helpful, especially when aiming for a self-learning system, configuring and calibration of the system and system reliability. The controlling means may be configured such that based on the data input provided by the sensors and the data input provided as feedback from the implanted, intra corporeal components of the active closed-loop medical system the control algorithm which is done by the control software of the control means can be configured as self-learning system, which uses all input to adapt the control algorithm continuously.

The communication between the components of the active closed-loop medical system may be established via a wireless radio-frequency link and/or a via wireless ultrasound link.

For example, a wireless radio-frequency link and/or a wireless ultrasound link may be used to establish a connection for data and/or signal transmission or any other connection between implanted components and non-implanted components of the system. Also, only implanted components of the system can be connected this way or only non-implanted components of the system can be connected this way.

Moreover, it is possible that the active closed-loop medical system comprises brain and/or neural signal receiving means, by means of which brain and/or neural signals may be received.

The signal receiving means may be connected to the controlling means such that the brain and/or neural signals are at least partially used for controlling the implantable medical device.

By this, the brain and/or neural signals may be used for controlling the system. This is especially beneficial for active closed-loop medical systems to restore neural control of the patient and when improving recovery after neurological disorders like spinal cord injury (SCI), for example after trauma, or other conditions like stroke or multiple sclerosis. By allowing influence in real-time of the patients brain and/or neural signals, the patients neurological paths are given an enhanced possibility to reset and regain the neurological paths in the patients body.

The active closed-loop medical system may further comprise a tapping signal control module configured to receive and process signal based on tapping commands that set the specific control signals and/or method steps of the closed-loop processing of the system, especially to stand and/or walk and/or sit to stand/stand up, move the arms and/or generally move parts of the body. Such a tapping signal control module is especially beneficial for paraplegic patients and will allow them an option for simple control signal input.

For example, tapping signal control module may comprise a sensor to detect signals based on tapping commands. Such a sensor may be (but not limited to) an accelerometer, a pressure sensor, an inductive sensor or the like. The signals based on tapping commands may be predetermined and defined signals that are recognized by the system, e.g. by detecting predefined patterns to e.g. distinguish from movement of the patient or other "noise" that is not intended to create a tapping command.

Also (additionally or alternatively), the tapping signal control module may comprise a smartphone or tablet PC (for example connected to one or more components of the system wirelessly via Bluetooth an/or wired), which allows the user to enter control signals for the system by means of tapping on the screen.

Moreover, the active closed-loop medical system may comprise an augmented reality module as part of the closed-loop system. In particular, the implantable medical device, the control means, the non-implanted component and the augmented reality module can be interlinked such that they form together the closed-loop system. The augmented reality module can provide a virtual environment or partial virtual environment. By this, the user of the system can use the system in an augmented reality environment. Specific trainings and movement proposals or movements can be provided. Also, support information can be displayed in the virtual environment. The augmented reality can be used to create a game-like environment to make training sessions for rehabilitation patients more interesting and/or to keep the patient motivated. For example, a game-like environment can be created, which motivates the patient to perform a specific sequence of movement in order to successfully complete a level of a game. So, the training session is less boring and the patient is kept motivated. For example, stepping and/or touching points could be displayed or projected onto the floor or a surface on and/or in a training site.

Especially and explicitly disclosed is a method of treating a patient by means of an active closed-loop medical system comprising at least one implantable medical device, at least one non-implanted component and at least a controlling means for controlling the implantable medical device, wherein the implantable medical device, the non-implanted component and the controlling means are connected for data exchange, wherein the implantable medical device, the non-implanted component and the controlling means are forming in the active state a closed-loop system in such that the implantable medical device is controlled by the controlling means on the basis of the signals exchanged with the non-implanted component. The active closed-loop medical system may be an active closed-loop medical system as set forth above and as specified in the claims of this application.

The method of treating a patient is especially a method of treating a patient with neurostimulation by means of an active closed-loop medical system.

FIG. 1 shows a person (e.g., patient) P within a training or living environment E and with an active closed-loop medical system 10.

The active closed-loop medical system 10 comprises external sensors S1, S2, S3, S4 and S6 and one implanted sensor S5. As used herein, external sensors may refer to sensors positioned outside a body of the person P.

Furthermore, there are receiver/sender (transceiver) units R1 and R2 for selected sensor signals.

Furthermore, there is a fixed sender/receiver R3 for collecting, processing and sensing all sensor data and/or control signals for the implant I. As shown in FIG. 1, the implant I is implanted within the body of the person P.

Also there is a portable sender/receiver R3', which is collecting, processing and sending all sensor data and/or control signals to the implant I.

The sender/receiver R3 and R3' may be provided both or alternatively to each other in the closed-loop medical system 10.

Moreover, there is the implant I which is receiving raw or pre-processed sensor data or control signals from S1 to S6 or R3 and/or R3'. The implant I is capable to process the received data and may react to the data/control signals in an active way; the communication is, in one example, bi-directional, meaning that the implant I can possibly communicate in its actual state, acknowledge the reception of data and provide feedback to the sender/receiver R3 and/or R3'.

The implant I is here an implantable neurostimulator, inter alia comprising an implantable pulse generator (IPG) and at least one implantable electrode array connected with the IPG.

The neurostimulator is here a part of the system 10 and an Epidural Electrical Stimulation (EES) neurostimulator.

In particular, the Epidural Electrical Stimulation (EES) neurostimulator 16 is arranged and configured as a spatially selective spinal implant, configured to work on the basis of temporally precise stimulation algorithms adjusted in a 'closed-loop' way using real-time motion feedback inputs as a part of the active closed-loop medical system.

The system 10 comprises a voice control module V configured to receive and process voice based commands that set the specific control signals and/or method steps of the closed-loop processing of the system, here to stand and/or walk and/or sit to stand/stand up, move the arms and/or generally move parts of the body.

The voice control module V may comprise or may be a sensor for example for detection of voice based commands that set the specific control signals and program features of the closed-loop processing, for example to stand, walk, sit to stand, move the arms and/or generally move parts of the body. Also, the non-implanted and/or implanted sensor (e.g. provided as part of the implantable medical device 10) may be a sensor for example for detection of voice based commands that set the specific control signals and program features of the closed-loop processing, for example to stand, walk, sit to stand, move the arms and/or generally move parts of the body.

The active closed-loop medical system 10 comprises a tapping signal control module TS configured to receive and process signal based on tapping commands that set the specific control signals and/or method steps of the closed-loop processing of the system, especially to stand and/or walk and/or sit to stand/stand up, move the arms and/or generally move parts of the body.

For example, tapping signal control module TS may comprise a sensor to detect signals based on tapping commands. Such a sensor may be (but not limited to) an accelerometer, a pressure sensor, an inductive sensor or the like. The signals based on tapping commands may be predetermined and defined signals that are recognized by the system 10, e.g. by detecting predefined patterns to e.g. distinguish from movement of the patient or other "noise" that is not intended to create a tapping command.

Also, here the tapping signal control module TS comprise mobile device MD, e.g. a smartphone or tablet PC (for example connected to one or more components of the system wirelessly via Bluetooth an/or wired), which allows the user to enter control signals for the system by means of tapping on the screen.

The implantable medical device is here formed by the implant I and the implanted sensor S5.

Moreover, the active closed-loop medical system may comprise an augmented reality module AR as part of the closed-loop system 10.

The augmented reality module AR is interlinked (e.g. wirelessly over W1 connected inter alia with receiver/sender units R1, R2, R3 or over W2 with inter alia the implant I and sensor S5 and/or via wired connection).

The augmented reality module AR comprises here augmented reality glasses which superpose virtual elements over the reality.

Moreover, the active closed-loop medical system 10 comprises brain and neural signal receiving means 12, by means of which brain and neural signals may be received.

The signal receiving means is connected to the controlling means such that the brain and neural signals are at least partially used for controlling the implantable medical device.

All components are shown in FIG. 1 form the active closed-loop medical system 10. The closed-loop medical system includes a control system 14 that includes the various sensors described herein (e.g., sensors S1-S6), a controller (which may be referred to herein as the controlling means), the implant I, and the various modules described herein (e.g., voice control module V, tapping signal control module TS, and augmented reality module AR). In one example, the controller is inter alia formed by the receiver/sender units R1, R2, R3 and R3'. The controller may additionally be formed by the brain and neural receiving means 12, which may be an electronic module of the controller, in one example.

The controller (e.g., the controlling means) may be an external device or partially internal and external device with an internal intelligence (i.e. software and processor unit). Specifically, the controller may be coupled to various components of the closed-loop medical system 10 to carry out the control routines and actions described herein (such as the control routine shown in FIG. 3, as described further below). For example, the controller may include a processor unit, input/output ports, an electronic storage medium for executable programs and calibration values, random access memory, keep alive memory, and/or a data bus. As depicted, the controller may receive input from a plurality of sensors, such as sensors S1-S6 and modules, such as modules AR, 12, TS, and V. The controller may also receive user inputs via additional wireless signals or connections. The controller may include one or more algorithms for analyzing the various signals received from the sensors, modules, and/or from received user inputs. Furthermore, controller may communicate with various components of the closed-loop medical system, such as the implant I. In some examples, the storage medium (e.g., memory) may be programmed with computer readable data representing instructions executable by the processor for performing the methods described below (with reference to FIG. 3) as well as other variants that are anticipated but not specifically listed.

As further shown in FIG. 2, the patient P may also move out of the training area and only by means of the sensor S6, which can be for example an accelerometer attached to the leg of the patient P, the portable sender/receiver R3' and the implant I (providing of sensor S5, which is implanted, is not necessary, but possible) can also form the minimal setup of the active closed-loop medical system 10.

Here, a wireless connection W1 between the sensor S6 and the sender/receiver R3' is provided. A further wireless connection W2 is provided transcutaneously between the sender/receiver R3' and the implant I.

The sensor S6 sends his signal over Bluetooth (and/or WIFI and/or inductive and/or via ultrasound) via the first wireless connection W1 to the receiver R3', which can be formed by a small PC with Bluetooth-transceiver or appropriate wireless interface.

In general, it would be also possible that additionally or alternatively the connection W1 is replaced by a wired connection or comprises additionally a wired connection. Also, an ultrasound connection could be established here alternatively or additionally, in order to form a redundant connection.

The receiver R3' processes the data and sends the control signals to the implant I via a coil-to-coil communication W2.

In the non-training environment of FIG. 2, the controller (e.g., controlling means) may include the portable sender/receiver R3'. The controller may additionally include the brain and neural signal receiving means. Additionally, in the environment of FIG. 2, the control system 14 may include the controller, the neural signal receiving means 12, the voice control module, implant I, tapping signal module TS, augmented reality module AR, sensor s6 and/or mobile device MD.

As shown in FIGS. 1 and 2, the components S1, S2, S3, S4, S6, R2, R1/S1, R3, R3' are arranged extra corporeal of the patient P.

The functional layout of the system can be described as follows:

By means of the active closed-loop medical system 10 as shown in FIGS. 1 and 2, a restoration and/or replacement and/or enhancement of the human sensory-motor system can be provided.

Especially, an active closed-loop medical system 10 that works in real-time (i.e. including a delay close to real-time between 0 to 30 ms) can be provided.

The embodiment shown in the figures allows to interlink the active components like a stimulator, an implantable pulse generator (IPG) which can be part of the implant or even an actuator inside of the body to be controlled based on measures taken at a certain distance from this component without wired connections.

In case of a real-time interaction, the person could for example be assisted in a task-institution-specific manner. This especially beneficial, when the person is trained in the post-trauma rehabilitation in order to help the patient P with recovery for example from spinal cord injury. As the overall system forms an active closed-loop medical system 10 that works in real-time, the system can react to unforeseen events instead of running a pre-defined routine.

By providing a voice control by means of the voice control module V the handling of the whole system for the user is simplified and can be more intuitive. Especially in cases, when the patient or the physician or the trainer of the patient intends to change the way or kind of movement, this can be triggered by a simple voice command.

As such, e.g. the patient P provided a spoken voice command like

"stand" or "stay" if standing is intended,

"walk", if walking is intended,

"sit to stand" or "stand up", if standing up is intended,

"move the right arm", "move left arm", "move both arms" if such a movement is intended, or suitable other commands for moving specific body parts of the patient. The voice control module V may be equipped with a basic configuration and a self-learning control system such that during the training the patient P is able to gain back more and more control.

Such a voice command is then received by the voice control module, transformed into a system signal configured to be processed by controlling means (e.g., controller of control system 14 shown in FIGS. 1 and 2) and submitted to the controlling means. This process may be done also in real-time.

Similar control over the system can be obtained by using the tapping signal control module TS:

The user may tap commands onto or close to a sensor or the mobile device MD of the tapping signal control module TS like "tap"—"no tap/break"—"tap", if standing is intended, "tap"—"tap"—"no tap/break"—"tap"—"tap", if walking is intended, "tap"—"no tap/break"—"tap"—"no tap/break"—"tap", if standing up is intended, suitable tap signals for "move the right arm", "move left arm", "move both arms" if such a movement is intended, or suitable other commands for moving specific body parts of the patient. These above commands only represent examples and can be replaced by other suitable examples.

The tapping signal control module TS may be equipped with a basic configuration and a self-learning control system such that during the training the patient P is able to gain back more and more control.

Such a tap command is then received by the tapping signal control module TS, transformed into a system signal configured to be processed by controlling means and submitted to the controlling means. This process may be done also in real-time.

By means of the neural signal receiving means (e.g., module) 12, the brain and neural signals may be used for controlling the system 10. In the embodiment shown in FIG. 1 and FIG. 2, this serves to restore neural control of the patient and when improving recovery after neurological disorders like spinal cord injury (SCI), for example after trauma, or other conditions like stroke or multiple sclerosis. By allowing influence in real-time of the patient's brain and/or neural signals, the patient's neurological paths are given an enhanced possibility to reset and regain the neurological paths in the patient's body.

The EES neurostimulator 16 does not directly stimulate the spinal cord, nor even the motor neuron comprised within the spinal cord, but the afferent sensory neurons prior to entering into the spinal cord, hence activating the synaptic circuits that are naturally involved in locomotor control.

Therefore, EES neurostimulator 16 specifically triggers activity dependent plasticity in the spinal cord resulting in ongoing learning and improvement of the patient's locomotor function.

So, by means of the EES provided by the system 10 with its EES neurostimulator 16 immediate and training-induced effects can be further improved when proprioceptive afferent nerves are stimulated more selectively and aligned with the different phases of the gait cycle. During walking, these phases consist of an alternation between stimulation of the extension and flexion muscles of the right versus the left leg. Time-space EES may be used to restore both the swing phase (flexion) and the weight-bearing stance phase (extension) whereas continuous EES may block the limbs.

The augmented reality module AR is used to enhance the training of the patient P. It can provide a virtual environment or partial virtual environment. By this, the user of the system can use the system in an augmented reality environment. Specific trainings and movement proposals or movements can be provided. Also, support information can be displayed in the virtual environment. The augmented reality can be used to create a game-like environment to make training sessions for rehabilitation patients more interesting and/or to keep the patient motivated. For example, a game-like environment can be created, which motivates the patient to perform a specific sequence of movement in order to successfully complete a level of a game. So, the training session is less boring and the patient is kept motivated. For example, stepping and/or touching points could be displayed or projected onto the floor or a surface on and/or in a training site (for this e.g. one or more additional projectors like beamers can be provided as part of the augmented reality module AR).

The controller of the control system 14 shown in FIGS. 1 and 2 may obtain feedback (e.g., feedback signals) from the various sensors S1, S2, S3, S4, S5 and S6. For example, the sensors S1, S2, S3, S4, S5 and S6 may obtain (e.g., measure) feedback signals, which can be neural signals, in particular cortical signals, recorded from sensory, motor, sensorimotor or pre-motor cortex. The feedback signals may be acquired in real-time. They can be neural signals and signals providing features of motion of said subject.

As feedback signals may be used inter alia but not limited to EMG responses, kinetic data, kinematic data, motion data, footswitch, pressure sensors, accelerometers and the respective signals, goniometers and the respective signals, barometers and the respective signals giroscopes and their respective signals.

In a kind of a self adjusting and self learning system and closed-loop control operation mode the feedback from the sensors S1 to S6 is used to update and to change the control signals being provided by the controller (e.g., controlling means). In this way, the feedback is used to adjust or control the control setup of the controller and wherever needed to overwrite the existing control routine.

As such, based on real-time feedback, e.g., motion feedback, control signals may be sent back by the sender and receiver units and updated on the basis of ongoing motion of the subject. In particular, as such the signals provided by the implanted neurostimulator are based on an updated control routine (updated control signals) provided by the controller.

Figure 3:
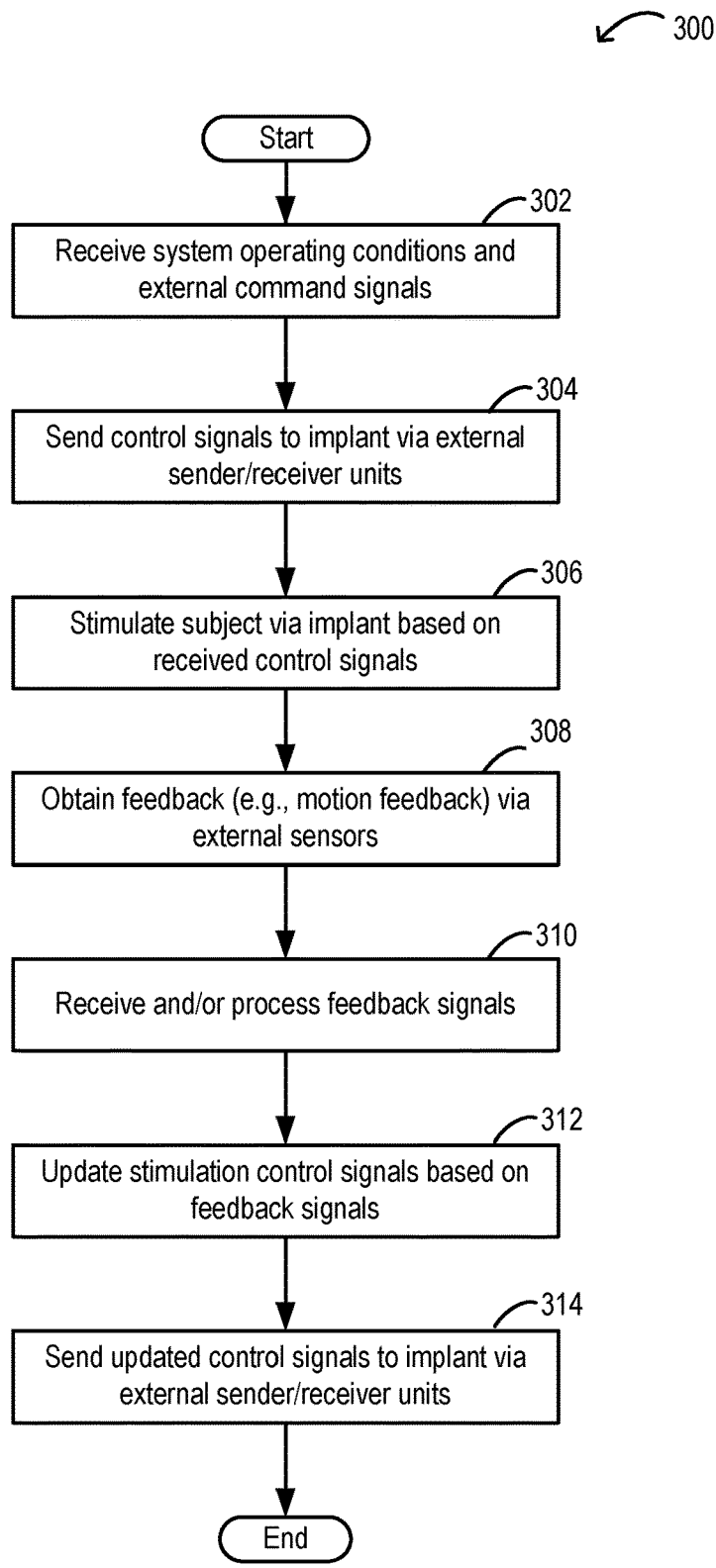
FIG. 3 shows a flow chart of a method for controlling a closed-loop medical system.

An example process for operating the systems shown in FIGS. 1 and/or 2 and updating stimulation control signals based on real-time feedback received from one or more sensors of the system is shown in method 300 of FIG. 3. Method 300 may be executed by and according to instructions stored on memory of a controller of the active closed-loop medical system, such as controller of control system 14 shown in FIGS. 1 and 2 in conjunction with signals received from various sensors of the control system, such as sensors S1-S6 shown in FIGS. 1 and 2.

Method 300 begins at 302 by receiving system operating conditions and external command signals (e.g., commands). The system operating conditions may include a power level (e.g., on/off state and/or battery power level) and/or signal strength of various components and/or wired or wireless connections between components of the closed-loop medical system. Additionally, various modules of the control system (e.g., voice control module V, augmented reality module AR, tapping signal control module TS, etc.) may receive commands from external sources, such as a mobile device or the patient (e.g., via tapping or voice commands). As one example, the voice control module may receive and process voice based commands that set the specific control signals of the closed-loop processing of the system, as introduced above. The sender/receiver units of the system (e.g., controller) may receive and process these commands and then determine control signals to be send to the implant based on these commands.

The method proceeds to 304 where the method may include sending sensor and/or control signals to the implant via the external sender/receiver units (e.g., one or more of sender/receiver units R1, R2, R3, and R3' shown in FIGS. 1 and 2). Then, at 306, the method includes stimulating the subject (e.g., patient) via the implant based on the received control signals. For example, in response to receiving the control signals at the implant, the implant may send corresponding stimulation signals to the subject via one or more electrodes or stimulations devices implanted within the subject.

At 308, the method includes obtaining (e.g., receiving) feedback (e.g., motion feedback) via the external sensors S1-S4 and S6 and/or implanted sensor S5. The sensors may be implanted and/or external, non-invasive sensors. For example, the external sensors may measure motion of the subject resulting from applying the stimulation commands to the subject at 306. The feedback signals obtained by the sensors are then sent to and received and/or processed by the controller, which may include one or more of the receiver/sender units at 310.

At 312, the method includes updating the stimulation control signals, at the controller, based on the received and processed feedback signals. For example, the controller may update the stimulation control signals in response to receiving the feedback signals. As one example, if a feedback signal indicates the subject's arm moved farther than anticipated, the controller may reduce the commanded stimulation signal for the subject's arm. In this way, the controller may determine the updated stimulation control signals as a function of the received feedback signals, according to instructions, algorithms, and/or look-up tables stored in memory of the controller. Then, at 314, the method may include sending the updated control signals to the implant via the external sender/receiver units. The implant may then stimulate the subject according to the updated control signals.

In this way, with regard to the feedback control-loop, the feedback signals from the sensors are processed in the controlling means (e.g., controller). For this, the controlling means comprises internal processors and calculating means which are capable to compare the obtained feedback with the existing control setup for the neurostimulator.

In case that the expected reaction and motion based on the currently used control setup is not matching to the feedback, an adjustment process is triggered by the controlling means. For this, the controlling means comprises control feedback signals, which are stored in a separate storage means. If the control signals, the respective expected feedback signals, and the obtained real-time feedback signals match to each other, no change is done by the controlling means. If the comparison reveals that an adjustment is necessary, such adjustment is done by the controlling means and than applied to the neurostimulator (e.g., implant).

Note that the example control and estimation routines included herein can be used with various neuromodulation and/or neurostimulation system configurations. The control methods and routines disclosed herein may be stored as executable instructions in non-transitory memory and may be carried out by the control unit in combination with the various sensors, actuators, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control unit, where the described actions are carried out by executing the instructions in a system including the various hardware components in combination with the electronic control unit.

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. An active closed-loop medical system, comprising:
at least one implantable medical device;
at least one non-implanted component; and
at least a controller for controlling the at least one implantable medical device, wherein the at least one implantable medical device, the at least one non-implanted component, and the controller are connected for data exchange, wherein the at least one implantable medical device, the at least one non-implanted component, and the controller form, in an active state, a closed-loop system where the at least one implantable medical device is controlled by the controller on the basis of signals exchanged with the at least one non-implanted component,
wherein the at least one non-implanted component comprises or is a sensor for sensing physiological data of a patient in which the at least one implantable medical device is implanted, and wherein the sensor is configured to acquire signals related to the physiological data, wherein the physiological data is one or more of kinetics, kinematics, muscular activity, neural activity, neural activity correlates, blood pressure, heart rate, and body temperature,
wherein the controller is configured such that signals exchanged with the controller from the at least one non-implanted component and/or the at least one implantable medical device are processed in real-time;
wherein the at least one implantable medical device comprises or is a neurostimulator, wherein the neurostimulator is an Epidural Electrical Stimulation (EES) neurostimulator; and
wherein the at least one implantable medical device is configured to alternate limb stimulation in accordance with a gait cycle.

2. The active closed-loop medical system according to claim 1, wherein the at least one non-implanted component and the controller are connected at least partially wirelessly and/or by means of a wired connection.

3. The active closed-loop medical system according to claim 1, wherein the controller is at least partially arranged extracorporeal.

4. The system according to claim 3, wherein feedback signals acquired by a real-time monitoring component are both neural signals and signals providing features of motion of the patient.

5. The active closed-loop medical system according to claim 1, wherein the sensor is configured and arranged to produce feedback signals and wherein the feedback signals are acquired by a real-time monitoring component as a part of the controller and are neural signals, including cortical signals recorded from a sensory, motor, sensorimotor, or pre-motor cortex.

6. The active closed-loop medical system according to claim 1, wherein the active closed-loop medical system further comprises at least one implanted sensor as a part of the at least one implantable medical device for sensing the physiological data of the patient in which the at least one implantable medical device is implanted.

7. The active closed-loop medical system according to claim 6, wherein the at least one implantable medical device has an intracorporeal data transmission unit comprising a data transmission coil, wherein a receiver also comprises a data transmission coil and wherein the receiver and the intracorporeal data transmission unit are transcutaneously connected by means of a coil-to-coil, or inductive coupling, communication connection provided by the data transmission coil of the receiver and the intracorporeal data transmission unit.

8. The active closed-loop medical system according to claim 6, wherein a receiver is connected in the active state with the at least one non-implanted component via one or more of a wireless radio-frequency link, wherein the wireless radio-frequency link is Bluetooth or WiFi, and a wireless ultrasound link.

9. The active closed-loop medical system according to claim 1, further comprising a voice control module configured to receive and process voice based commands that set control signals for controlling the at least one implantable medical device, wherein the control signals include signals to stand, walk, sit, stand up, move arms, and/or move alternate parts of a body of the patient in which the at least one implantable medical device is implanted.

10. The active closed-loop medical system according to claim 1, further comprising extracorporeal communication means, wherein the extracorporeal communication means comprise a receiver, which is wireless or wired connected in the active state with the at least one non-implanted component.

11. The active closed-loop medical system according to claim 1, wherein communication between components of the active closed-loop medical system is either uni-directional or bi-directional and/or established via a wireless radio-frequency link and/or via a wireless ultrasound link.

12. The active closed-loop medical system according to claim 1, further comprising a brain and/or neural signal receiving module, where brain and/or neural signals may be received, and wherein the brain and/or neural signal receiving module is connected to the controller such that the brain and/or neural signals are at least partially used for controlling the at least one implantable medical device.

13. The active closed-loop medical system according to claim 1, further comprising a tapping signal control module configured to receive and process signal based tapping commands that set specific control signals of closed-loop processing of the system, including to stand, walk, sit, stand up, and move arms of the patient in which the at least one implantable medical device is implanted, and/or move an alternate part of a body of the patient.

14. The active closed-loop medical system according to claim 1, further comprising an augmented reality module in communication with the controller and configured to provide a virtual environment or a partial virtual environment to the patient in which the at least one implantable medical device is implanted and provide movement commands to the controller.

15. A method for treating impaired locomotor function comprising an active, closed-loop medical system, comprising:
sending stimulation control signals to an implantable medical device implanted within a subject with impaired locomotor function via a controller;
stimulating the subject via the implantable medical device, according to the sent stimulation control signals to treat the impaired locomotor function;
during stimulation of the subject, obtaining motion feedback signals via one or more sensors in electronic communication with the controller;
processing the obtained motion feedback signals at the controller; and
updating the stimulation control signals based on the processed motion feedback signals,
wherein the stimulation control signals are updated based on real-time feedback received from the one or more sensors, and
wherein the implantable medical device stimulates via Epidural Electrical Stimulation (EES).

16. The method of claim 15, wherein the stimulation control signals are determined based on command signals received from one or more of a voice control module and a tapping signal control module.

17. An active closed-loop medical system, comprising:
an implantable medical device including a neurostimulator;
a non-implanted component including one or more external sensors; and
a controller electronically connected for data exchange with the implantable medical device and the non-implanted component and including memory with computer readable instructions for:
sending stimulation control signals to the implantable medical device, wherein the implantable medical device stimulates proprioceptive afferent nerves;
receiving motion feedback signals measured by the non-implanted component during stimulation of a subject in which the implantable medical device is implanted according to the sent stimulation control signals; and
updating the stimulation control signals sent to the proprioceptive afferent nerves based on the received motion feedback signals;
wherein signals exchanged with the controller from the non-implanted component and/or the implantable medical device are processed in real-time, and
wherein the neurostimulator is an Epidural Electrical Stimulation (EES) neurostimulator.

18. An active medical system, comprising:
at least one implantable medical device;
at least one non-implanted component; and
at least a controller for controlling the at least one implantable medical device, wherein the at least one implantable medical device, the at least one non-implanted component, and the controller are connected for data exchange, wherein the at least one implantable medical device, the at least one non-implanted component, and the controller form, in an active state, a system where the implantable medical device is controlled by the controller on the basis of signals exchanged with the at least one non-implanted component to alternate stimulation of extension and flexion muscles of a right leg versus a left leg in accordance with a gait cycle,
wherein the at least one non-implanted component comprises or is a sensor for sensing physiological data of a patient in which the at least one implantable medical device is implanted, and wherein the sensor is configured to acquire signals related to the physiological data, wherein the physiological data is one or more of kinetics, kinematics, muscular activity, neural activity, neural activity correlates, blood pressure, heart rate, and body temperature, wherein the controller is configured such that signals exchanged with the controller from the at least one non-implanted component and/or the at least one implantable medical device are processed in real-time, and wherein the at least one implantable medical device comprises or is a neurostimulator, wherein the neurostimulator is an Epidural Electrical Stimulation (EES) neurostimulator.

19. An active closed-loop medical system, comprising:

at least one implantable medical device;

at least one non-implanted component; and at least a controller for controlling the at least one implantable medical device, wherein the at least one implantable medical device, the at least one non-implanted component, and the controller are connected for data exchange, wherein the at least one implantable medical device, the at least one non-implanted component, and the controller form, in an active state, a closed-loop system where the at least one implantable medical device is controlled by the controller on the basis of signals exchanged with the at least one non-implanted component, wherein the at least one non-implanted component comprises or is a sensor for sensing physiological data of a patient in which the at least one implantable medical device is implanted, and wherein the sensor is configured to acquire signals related to the physiological data, wherein the physiological data is one or more of kinetics, kinematics, muscular activity, neural activity, neural activity correlates, blood pressure, heart rate, and body temperature, wherein the controller is configured such that signals exchanged with the controller from the at least one non-implanted component and/or the at least one implantable medical device are processed in real-time;

wherein the at least one implantable medical device comprises or is a neurostimulator, wherein the neurostimulator is an Epidural Electrical Stimulation (EES) neurostimulator; and wherein the at least one implantable medical device is configured to regulate blood pressure or heart rate.

* * * * *